(12) United States Patent
Matsushita et al.

(10) Patent No.: US 8,300,767 B1
(45) Date of Patent: *Oct. 30, 2012

(54) WAVELENGTH-CLASSIFYING TYPE X-RAY DIFFRACTION DEVICE

(75) Inventors: Kazuyuki Matsushita, Ome (JP); Takuto Sakumura, Hachioji (JP); Yuji Tsuji, Hamura (JP); Masataka Maeyama, Ome (JP); Kimiko Hasegawa, Hamura (JP)

(73) Assignee: Rigaku Corporation, Akishima-Shi, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/540,652

(22) Filed: Jul. 3, 2012

Related U.S. Application Data

(63) Continuation of application No. 13/170,708, filed on Jun. 28, 2011.

(30) Foreign Application Priority Data

Jun. 29, 2010 (JP) .................................. 2010-148384

(51) Int. Cl.
*G01N 23/207* (2006.01)
(52) U.S. Cl. ........................................... 378/73; 378/70
(58) Field of Classification Search ............... 378/70–73, 378/143, 144
See application file for complete search history.

(56) References Cited

U.S. PATENT DOCUMENTS

| | | | |
|---|---|---|---|
| 3,743,841 A | 7/1973 | Herglotz | |
| 5,491,738 A | 2/1996 | Blake et al. | |
| 2011/0317813 A1* | 12/2011 | Matsushita et al. | 378/73 |

FOREIGN PATENT DOCUMENTS

| | | | |
|---|---|---|---|
| JP | 5-89809 | A | 4/1993 |
| JP | 5-135722 | A | 6/1993 |
| JP | 5-152091 | A | 6/1993 |
| JP | 5-325851 | A | 12/1993 |
| JP | 6-215710 | A | 8/1994 |
| JP | 7-73831 | A | 3/1995 |
| JP | 8-94547 | A | 4/1996 |
| JP | 11-339703 | A | 12/1999 |
| JP | 2002-39970 | A | 2/2002 |
| JP | 2007-323964 | A | 12/2007 |
| JP | 4074874 | B2 | 4/2008 |
| JP | 2010-38722 | A | 2/2010 |

OTHER PUBLICATIONS

Search Report dated Sep. 28, 2011, issued in the corresponding United Kingdom Patent Application No. GB1110936.0.

* cited by examiner

*Primary Examiner* — Courtney Thomas
(74) *Attorney, Agent, or Firm* — Buchanan Ingersoll & Rooney PC

(57) ABSTRACT

A wavelength-classifying type X-ray diffraction device bombards a sample with characteristic X-rays generated from an X-ray generation source, and detects characteristic X-rays diffracted by the sample using an X-ray detector. The X-ray generation source is composed of several metals of different atomic number, respective metals generating several characteristic X-rays of different wavelengths. An X-ray detector is composed of several pixels for receiving X-rays and outputting pulse signals corresponding to X-ray wavelengths. Pixels are respectively furnished with classification circuits. The classification circuits classify and output pixel output signals based on each of characteristic X-ray wavelengths. X-ray intensity is detected on a per-wavelength basis in individual pixels 12. Measurement data based on different wavelength X-rays are acquired simultaneously in just one measurement. Data of diffracted X-rays of different wavelengths are acquired using the entire region of the receiving surface of a two-dimensional detector.

7 Claims, 12 Drawing Sheets

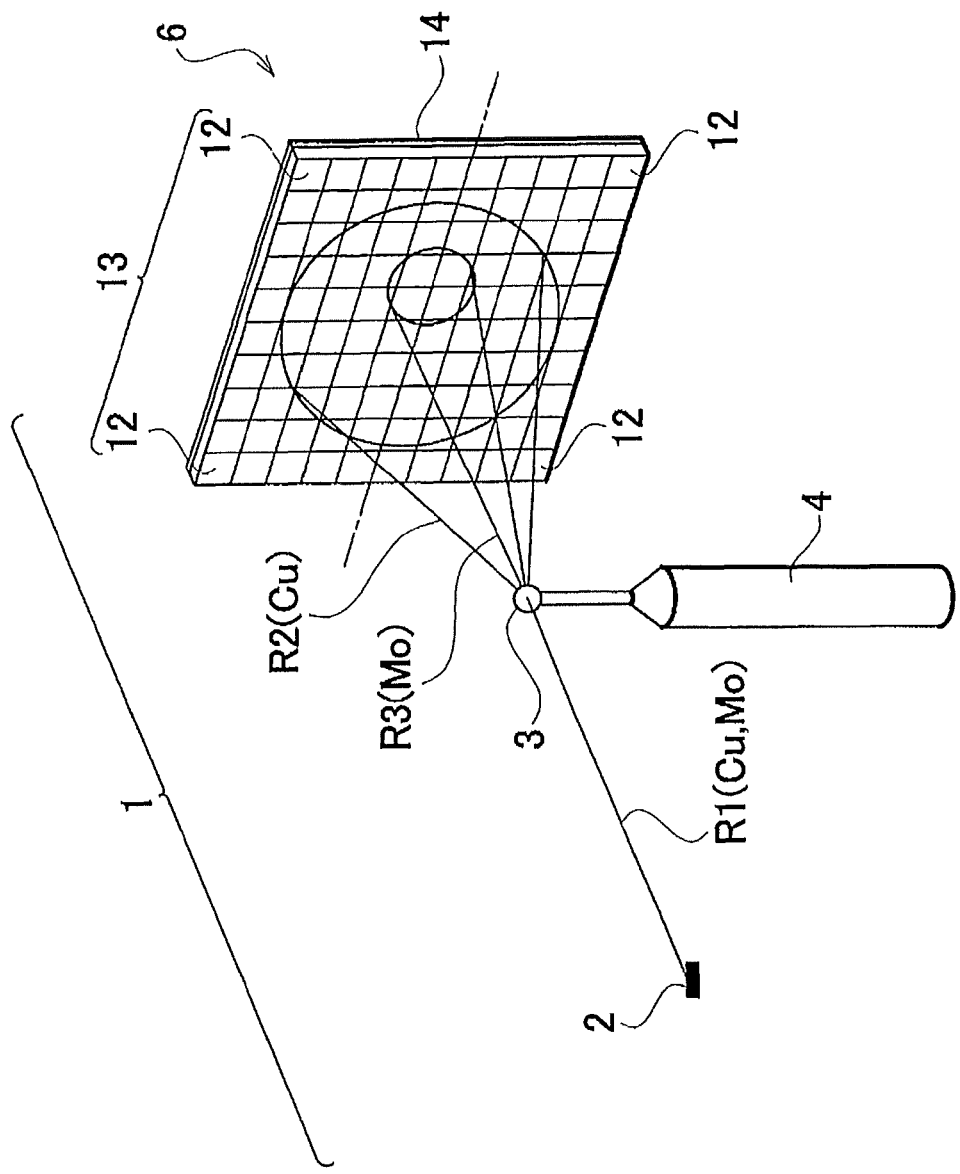

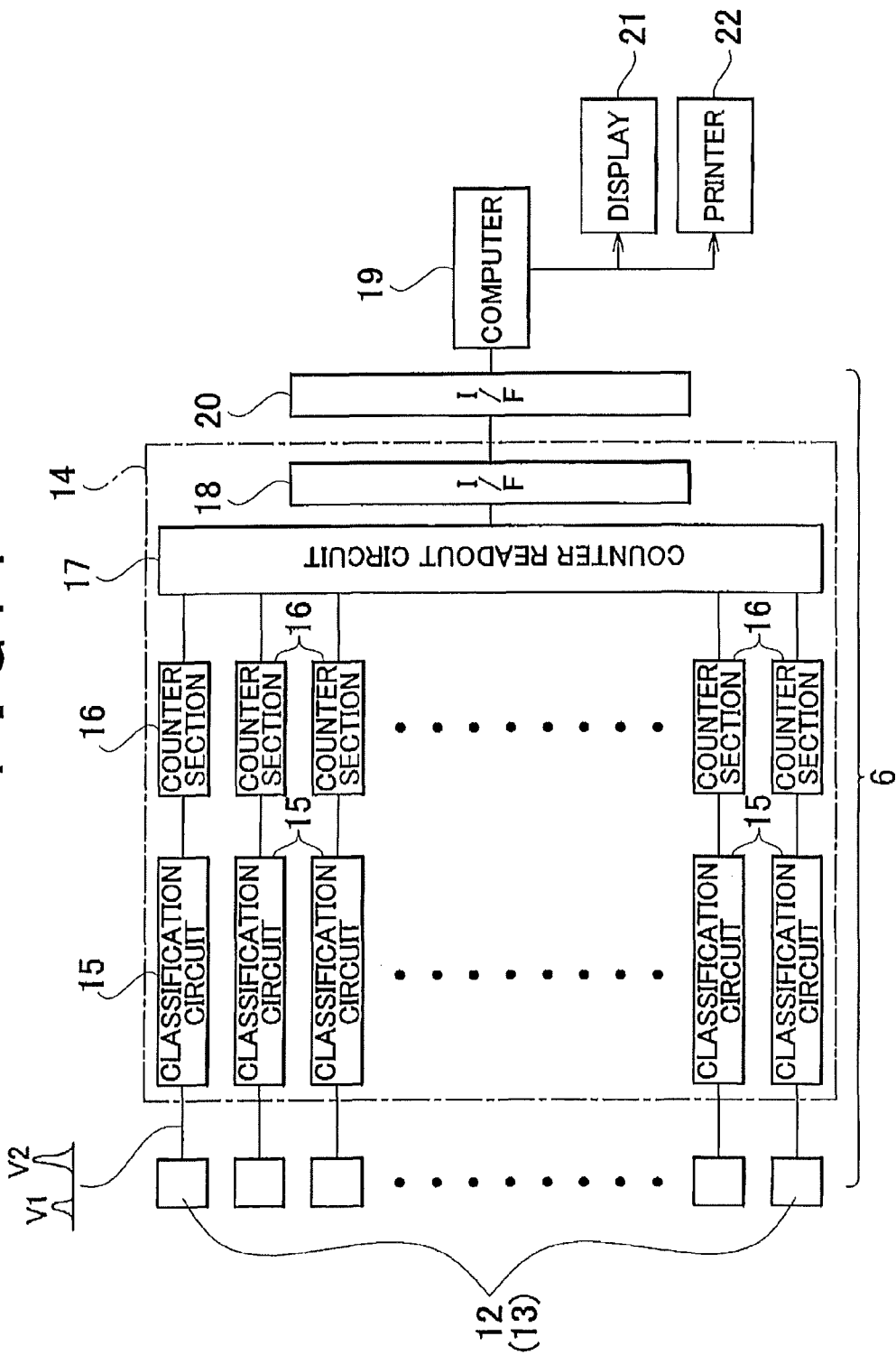

DIFFRACTED IMAGE OBTAINED WHEN BOTH
Mo-RAY AND Cu-RAY ARE INCIDENT ON A SAMPLE

DIFFRACTED IMAGE OBTAINED WHEN
Cu-RAY IS INCIDENT ON A SAMPLE

DIFFRACTED IMAGE OBTAINED WHEN
Mo-RAY IS INCIDENT ON A SAMPLE

R-Configuration

S-Configuration

WAVELENGTH-CLASSIFYING TYPE X-RAY DIFFRACTION DEVICE

BACKGROUND OF THE INVENTION

1. Field of the Invention

The present invention relates to an X-ray diffraction device of a wavelength-classifying type, having a function whereby X-rays that include a plurality of X-rays of different wavelengths may be classified into X-rays of each of the wavelengths, and X-ray measurements may be carried out using X-rays of the individual wavelengths.

2. Description of the Related Art

In the field of X-ray diffraction devices, there are instances in which it is desired to use a plurality of characteristic X-rays of different wavelengths when measuring a single substance to be measured. For example, for analysis in situations where the wave vector of the X-rays necessitates large radial range (for example, as in radial distribution analysis), or in the case of the multi-wavelength anomalous dispersion (MAD) method used in analyzing the structures of native proteins, there are instances in which a plurality of X-rays of different wavelengths are desired.

Hitherto, one procedure employed in instances where a plurality of X-rays of different wavelengths are used in an X-ray diffraction device involves swapping out the X-ray tube. The operation to swap out the X-ray tube is typically a manual operation performed by the operator. Because of this, problems have been encountered in regard to the considerable time needed for the swap out, and the difficultly of adjusting the emission optical path of the X-rays subsequent to swap out.

In particular, in the case of a demountable X-ray tube, which is a tube that uses a rotating anti-cathode, namely, a rotor target, as the anti-cathode, namely, as the target, swapping out the demountable X-ray tube requires first releasing the vacuum in the vacuum chamber in which the demountable X-ray tube is disposed, before swapping the tube out; and subsequently carrying out an operation to reestablish a vacuum state. In such instances, an extremely long period of time is needed before the vacuum chamber interior can be restored to a degree of vacuum enabling generation of X-rays.

Also, because demountable X-ray tubes are quite heavy, a risk is presented in regard to the demountable X-ray tube being dropped during the replacement operation, or of the demountable X-ray tube coming into contact with the device chassis. Another risk is that coolant introduced into the interior of the X-ray tube will drip down into the vacuum chamber interior during the swap-out operation of the X-ray tube.

Furthermore, in many instances, once the X-ray tube is replaced, the position of the X-ray generation source will be very slightly shifted out of position for reasons relating to the accuracy of mechanical attachment, and it has therefore been necessary to make readjustments to the optical system for measurement, which is supported by a goniometer inside the X-ray diffraction device.

Because operations to replace X-ray tubes are extremely laborious and time-consuming as discussed above, the operational efficiency of replacing a plurality of X-ray sources in a single X-ray generation device is extremely poor.

On the other hand, in instances of using a plurality X-rays of different wavelengths in an X-ray diffraction device, one method involves preparing an X-ray generation device for each of a plurality of X-ray sources of different wavelengths. However, a single X-ray generation device is quite expensive, making it extremely difficult to provide a plurality of these devices.

Furthermore, in instances where a substance being measured is a substance unable to maintain crystal structure for an extended period, the crystal structure may change during replacement of the X-ray tube or in the course of conducting measurements multiple times, so that sometimes accurate measurement data cannot be obtained.

To address the aforementioned problems, there have been proposed a multitude of X-ray generation devices adapted to generate a plurality of types of X-rays simultaneously, or to periodically switch among generating a plurality of types of X-rays. For example, one known device of this kind is an X-ray generation device that uses a so-called stripe target. With an ordinary rotating anti-cathode (namely, a rotor target), a metal of the same given type is deposited uniformly on a round tubular metal face which constitutes the X-ray generating section. With a stripe target, on the other hand, two or more different types of metal are deposited to predetermined width in cyclically alternating fashion (namely, in a stripe pattern) along the direction in which thermal electrons scan the surface of the target.

When this stripe target is rotated at high speed, X-rays of different wavelengths that correspond to the different types of metal can be elicited in a constant cycle. X-rays having wavelengths used for measurement can then be sorted using an analyzing crystal (namely, a monochromator). In an instance of changing the wavelength, the analyzing crystal is rotated about its own centerline to change the angle with respect to the impinging X-rays, or the analyzing crystal is exchanged for one of a different type.

In a known method according to Japanese Patent Laid Open Publication No. H7-073831, in place of a wavelength classification method that uses an analyzing crystal, diffracted X-ray data are acquired only at times of X-rays from the same given metal, in synchronization with rotation of a stripe target. Another method according to Japanese Patent Laid Open Publication No. H5-152091 teaches classification of X-ray wavelengths by opening and closing of a rotating shutter in synchronization with rotation of a stripe target.

Yet another method according to Japanese Patent Laid Open Publication No. H11-339703 teaches disposing ring shapes, namely, annular shapes, of two or more different metals along a direction perpendicular to the direction in which the thermal electrons scan the surface of the target, and classifying X-ray wavelengths by changing the electron emission angle of the electron gun. Still another method according to Japanese Patent Laid Open Publication No. 2007-323964 teaches disposing ring shapes of two or more different metals along a direction perpendicular to the direction in which the thermal electrons scan the surface of the target, and classifying X-ray wavelengths through parallel travel of the electron gun.

Another method according to Japanese Patent Laid Open Publication No. H5-089809 teaches disposing ring shapes of two or more different metals along a direction perpendicular to the direction in which the thermal electrons scan the surface of the target, and classifying X-ray wavelengths through travel of the target relative to the electron gun. Yet another method according to Japanese Patent Laid Open Publication No. H5-135722 teaches disposing ring shapes of two or more different metals along a direction perpendicular to the direction in which the thermal electrons scan the surface of the target, and classifying X-ray wavelengths by changing the direction of advance of the electron beam to change the metal being struck by the electrons.

In a device according to Japanese Patent Laid Open Publication No. H6-215710, ring shapes of two or more different metals are disposed, electron guns are disposed facing the individual different metals, and X-rays of different wavelengths are generated simultaneously while a plurality of types of measurement are carried out simultaneously using the X-rays. Also, in a known target for generating X-rays of different wavelengths according to Japanese Patent Laid Open Publication No. H5-325851, the target is formed of an alloy which is a combination of different metals.

In a known X-ray generation device according to Japanese Patent Laid Open Publication No. H8-094547, a plurality of X-ray tubes are provided for generating X-rays of different wavelengths, and control means are provided for controlling operation of these X-ray tubes under individually appropriate conditions. In a known X-ray diffraction device according to Japanese Patent Laid Open Publication No. 2002-039970, a plurality of X-ray tubes are provided for generating X-rays of different wavelengths, X-rays are caused to impinge on a sample from different directions, and a plurality of types of diffracted X-rays arising from X-rays of different wavelengths are received by a two-dimensional X-ray detector as they are emitted from the sample.

Further, in a known X-ray diffraction device according to Japanese Patent No. 4074874, X-rays of mutually different wavelengths are elicited respectively from an upper half region and a lower half region of a rotating target, and these bombard a single sample, whereupon diffracted X-rays emitted from an upper half region and diffracted X-rays emitted from a lower half region of the sample are detected simultaneously by a two-dimensional CCD detector. According to this device, measurement data based on X-rays of different wavelengths can be obtained simultaneously through just one measurement.

SUMMARY OF THE INVENTION

As described above, X-ray diffraction devices known in the prior art generate X-rays of a plurality of wavelengths either simultaneously or individually, while diffracted X-ray data are measured on the basis of the respective X-rays. However, because the detectors for detecting the diffracted X-rays lack the ability to distinguish between wavelengths, diffracted X-rays cannot be detected simultaneously while distinguishing among them in terms of their wavelengths (namely, in terms of their energies); rather, detection of diffracted X-rays has been carried out through sorting of the source of one specified X-ray wavelength only, and individually measuring each single X-ray wavelength.

With this method, X-rays of wavelengths that make no contribution to measurement are consumed needlessly. For this reason, problems such as waste of energy and accelerated wear of the target are encountered. Also, measurements made with X-rays of different wavelengths unavoidably have to be carried out in individual time slots, resulting in the problem of extended measuring times.

With a conventional X-ray diffraction devices, the extended measuring times meant that substances unable to maintain crystal structure for an extended period have been impossible to measure.

Japanese Patent No. 4074874 discloses an invention involving a time delay integration (TDI) operation in which a semiconductor detector of charge integration design, such as a two-dimensional charge coupled device (CCD) detector, is divided into an upper half region and a lower half region for use, thereby making possible simultaneous measurement of diffracted X-rays of different wavelengths. However, in this invention, there are encountered a number of problems, such as that the detection regions of the upper and lower halves are close to one another with each region having constricted surface area; measuring time is limited by the readout speed of intensity data; and a limited effective dynamic range results in susceptibility to becoming saturated easily.

With the foregoing in view, it is an object of the present invention to enable measurement data based on X-rays of different wavelengths in an X-ray diffraction device to be acquired simultaneously through just one measurement, and thereby to prevent waste of energy and wear of the target within a short time, as well as to enable measurement data based on X-rays of different wavelengths to be acquired in a short time.

Yet another object of the present invention is to make possible acquisition of diffracted X-ray data of different wavelengths using the entire region of the light-receiving face of a one-dimensional X-ray detector or a two-dimensional X-ray detector, so that highly reliable diffracted X-ray data may be obtained.

The wavelength-classifying type X-ray diffraction device according to the present invention is a wavelength-classifying X-ray diffraction device for bombarding a sample with characteristic X-rays generated by X-ray generating means, and detecting using X-ray detecting means the characteristic X-rays that are diffracted by the sample. The X-ray generating means is made of several different, namely, a plurality of, metals having different atomic numbers, and generates from the respective metals a plurality of characteristic X-rays of mutually different wavelengths. The X-ray detecting means is made of a plurality of pixels that receive the characteristic X-rays of a plurality of wavelengths diffracted by the sample and that output signals, for example, pulse signals, corresponding to the wavelengths of the respective characteristic X-rays. The pixels are respectively furnished with classifying means, the classifying means being adapted to classify output signals, for example, output pulse signals, of the pixels into each of the wavelengths of the characteristic X-rays, and output the signals.

In a known semiconductor X-ray detector according to Japanese Patent Laid Open Publication No. 2010-038722, which is adapted to output an electrical signal upon receiving an X-ray, the semiconductor X-ray detector has a function of outputting an electrical signal depending on the energy of the received X-ray (namely, the wavelength of the X-ray) (herein also referred to as energy resolution). This detector also has a function of discriminating, namely, sorting, the X-rays on the basis of the amount of energy from an upper limit value and a lower limit value of the value of pulse height, and through this discrimination function is able to eliminate the background component in a diffracted X-ray profile.

However, Japanese Patent Laid Open Publication No. 2010-038722 does not disclose bombarding a sample with X-rays of different wavelengths. Also, whereas Japanese Patent Laid Open Publication No. 2010-038722 discloses a silicon strip detector having a function of eliminating wavelength components that correspond to the background, the publication does not disclose the pixel array detector according to the present invention, namely, a detector composed of a plurality of pixels which are individually endowed with a function of classifying a plurality of X-rays that bombard a sample, the X-rays having mutually different wavelengths.

Japanese Patent Laid Open Publication No. 8-299318 discloses a technique for bone densitometry using X-rays, wherein a living body, namely, an organism, is bombarded with a plurality of types of characteristic X-rays of different wavelengths; the X-rays that pass through the living body are detected by a semiconductor detector; output signals of the semiconductor detector are discriminated on a per-wavelength basis by a plurality of types of pulse height discriminating circuits; and computations of bone density are carried out in relation to X-rays of the individual discriminated wavelengths.

However, the technique disclosed in this publication relates to the field of measuring bone density, and thus the technical field to which the publication relates is completely different from the field of measuring X-ray diffraction as in the present invention. That is, Japanese Patent Laid Open Publication No. 8-299318 contains no disclosure that could be considered to anticipate classification of a plurality of diffracted X-rays of different wavelengths that are emitted from a sample. Moreover, the publication does not touch upon a unique characteristic of the pixel array used in the present invention, namely, that of furnishing a pulse height discriminating circuit to every pixel of a one-dimensional or two-dimensional semiconductor detector.

In the wavelength-classifying type X-ray diffraction device according to the present invention, a diffracted X-ray beam containing diffracted X-rays of different wavelengths is detected by a pixel array detector in which every pixel is given a wavelength classifying function, and therefore despite the presence of a combination of diffracted X-rays of different wavelengths in the diffracted X-ray beam, diffracted X-rays may be detected and classified according every wavelength. Because of this, measurement data based on X-rays of different wavelengths can be acquired simultaneously and classified through just one measurement. In so doing, waste of energy can be prevented, wear of the target within a short time can be prevented, and measurement data based on X-rays of different wavelengths can be acquired in a short time. Because measurements are completed within a short time, measurements can be carried out without problems, even on substances which are unable to maintain crystal structure for extended periods.

Moreover, in the wavelength-classifying type X-ray diffraction device according to the present invention, rather than dividing the two-dimensional receiving surface of the X-ray detector and receiving diffracted X-rays of different wavelengths in each of these divided regions, diffracted X-rays of different wavelengths are instead respectively received over the entire region of the receiving surface of the X-ray detector, and therefore data of a plurality of diffracted X-rays of different wavelengths can be respectively acquired over a wider range, and highly reliable diffracted X-ray data can be obtained as a result.

By adopting a configuration whereby measurement data for every classified wavelength is saved on a per-wavelength basis to memory, and then image information is generated on the basis of the per-wavelength basis measurement data and supplied to image display means, for example, a flat panel display, the measurement results can be displayed on a per-wavelength basis on the image display means, or a combination of measured results for different wavelengths may be displayed on the image display means.

Optionally, the wavelength-classifying type X-ray diffraction device according to the present invention comprises counters for counting the number of signals, for example, pulse signals, that have been classified by the classifying means for every wavelength. Through these counters, the intensity of diffracted X-rays in relation to X-rays of the individual wavelengths can be represented by the magnitude of counter values.

Optionally, the wavelength-classifying type X-ray diffraction device according to the present invention comprises computing means for computing relational values of diffracted X-ray wavelength, diffraction angle, and intensity, on the basis of positions of diffracted X-rays detected by the X-ray detecting means, and the counted value of every wavelength of diffracted X-rays detected by the classifying means. In so doing, a diffracted X-ray diagram, namely, a diffracted X-ray profile, that represents a relationship between diffraction angle and diffraction intensity of diffracted X-rays can be represented on a per-wavelength basis.

Optionally, in the wavelength-classifying type X-ray diffraction device according to the present invention, the X-ray generating means can be constructed using a rotor target made of a plurality of different metals disposed in alternating fashion along an electron scanning direction. Because this rotor target is provided with a striped pattern of different metals on the target surface, it is called a stripe target. This target is also called a zebra target.

Alternatively, the X-ray generating means is constructed using a rotor target made of a plurality of different metals disposed in respectively continuous fashion along the electron scanning direction, the metals being disposed adjacently to one another in a direction perpendicular to the electron scanning direction.

Optionally, the X-ray generating means is constructed of a first X-ray generating section for generating X-rays of a first wavelength, and a second X-ray generating section for generating X-rays of a second wavelength different from the first wavelength. The first X-ray generating section and the second X-ray generating section are arranged at mutually different positions, and are respectively arranged at positions such that a given sample can be bombarded with X-rays.

Further, the electron receiving surface (namely, the X-ray generating surface) of the rotor target can be formed by an alloy which is a mixture of different metals.

In the wavelength-classifying type X-ray diffraction device according to the present invention, optionally, the X-ray detecting means is a two-dimensional pixel array detector made of a plurality of pixels lined up two-dimensionally and having a reception surface area capable of detecting a plurality of types of diffracted X-rays of different wavelengths. Alternatively, the X-ray detector is a one-dimensional pixel array detector made of a plurality of pixels lined up one-dimensionally and having reception length enabling a plurality of diffracted X-rays of different wavelengths to be detected.

A two-dimensional pixel array detector can acquire diffracted X-ray information at each of positions in a perpendicular direction to the equatorial plane. A one-dimensional pixel array detector integrates, namely, combines, diffracted X-ray information of a perpendicular direction to the equatorial plane.

The wavelength-classifying type X-ray diffraction device according to the present invention is favorably used for structure analysis of samples having small molecular mass and including a heavy atom. Examples of heavy atoms are Fe, Co, Mo, and W. Small molecular mass refers to substances of low molecular weight, and these are typically substances with lattice length of 20 Å or smaller. In the case of structure analysis, the X-rays of different wavelengths may be CuKα rays (wavelength 1.542 Å) and MoKα rays (wavelength 0.711 Å). Specifically, the initial structure can be determined using CuKα rays, while using MoKα rays for refining of the structure.

The wavelength-classifying type X-ray diffraction device according to the present invention is favorably used for determining absolute structure of a molecule having optical activity. In this case, the X-rays of different wavelengths may be CuKα rays (wavelength 1.542 Å) and MoKα rays (wavelength 0.711 Å), with the Flack parameter being derived using CuKα rays, and refining of the structure being carried out using MoKα rays.

The wavelength-classifying type X-ray diffraction device according to the present invention is favorably used for structure analysis of proteins. In this case, the X-rays of different wavelengths may be CuKα rays (wavelength 1.542 Å), CoKα rays (wavelength 1.7892 Å), and CrKα rays (wavelength 2.290 Å), and the phase of the crystal structure factor can be derived based on a known MAD method.

Alternatively, the X-rays of different wavelengths using CrKα rays and CuKα rays, the phase of the crystal structure factor can be determined based on the known single-wavelength anomalous dispersion (SAD) method using CrKα rays, and measurements of diffracted X-ray intensity may be refined using CuKα rays, which are characteristic X-rays.

The wavelength-classifying type X-ray diffraction device according to the present invention is favorably used for structure analysis of powder samples. In this case, the X-rays of different wavelengths can be CuKα rays and MoKα rays, the lattice constant can be determined based on a diffraction profile obtained using CuKα rays, and refining of the crystal structure can be carried out on the basis of a diffraction profile obtained using MoKα rays.

BRIEF DESCRIPTION OF THE DRAWINGS

FIG. 1 is a perspective view showing an embodiment of the wavelength-classifying type X-ray diffraction device according to the present invention.

FIG. 4 is a block diagram showing an embodiment of a control system constituting another principal section of the device of FIG. 1.

DESCRIPTION OF THE PREFERRED EMBODIMENTS

First Embodiment

Figure 2A:
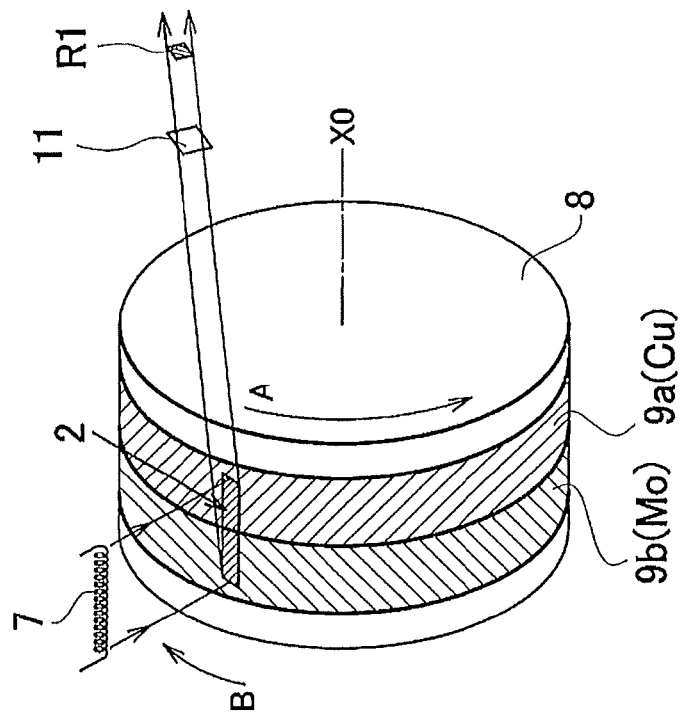
FIG. 2A is a perspective view showing an embodiment (point focus) of an X-ray generating section constituting a principal section of the device of FIG. 1.

The embodiments of the wavelength-classifying type X-ray diffraction device according to the present invention are described below. It should be noted that the present invention is not limited to the following embodiment. While the following description makes reference to the drawings, in some instances, constituent elements may be depicted in the drawings at proportions different from the actual ones in order to aid understanding of characteristic portions.

FIG. 1 shows an embodiment of the wavelength-classifying type X-ray diffraction device according to the present invention. This wavelength-classifying type X-ray diffraction device 1 has an X-ray focal spot 2 provided as X-ray generating means for generating X-rays, a sample support device 4 supporting a sample 3, and an X-ray detector 6 for detecting diffracted X-rays emitted from the sample 3.

As shown in FIG. 2A for example, the X-ray focal spot 2 is formed as a region where an electron flux emitted from a filament 7 constituting a cathode collides with the outside peripheral face of a rotor target 8 constituting the anti-cathode. In order to prevent damage from occurring in the region of the X-ray focal spot 2, the rotor target 8 is driven by a drive device, not shown, and rotates about its own center line X0 as shown by arrow A. Because of this, the direction in which electrons scan the surface of the rotor target 8 is the opposite direction from the rotation direction of the rotor target 8, as shown by arrow B.

When electrons collide with the X-ray focal spot 2, X-rays are emitted from the X-ray focal spot 2. An X-ray R1 is then emanated to the outside from an X-ray window 11 which is provided in a dividing wall (not shown) enclosing the rotor target 8. This X-ray R1 bombards the sample 3 (see FIG. 1). In the present embodiment, of the X-rays emitted from the X-ray focal spot 2, the X-ray R1 is the X-ray that emanates from a short side of the X-ray focal spot 2 to form an X-ray beam with a cross sectional shape that is circular or a rectangular dot, known as point focus.

On the outside peripheral face of the rotor target 8 there are provided a plurality of different metals (in the present embodiment, two) having mutually different atomic numbers, namely, a first metal 9a and a second metal 9b. The first metal 9a is Cu (copper) for example, and the second metal 9b is Mo (molybdenum) for example. The metals 9a and 9b are respectively continuous along the direction in which the electrons from the filament 7 scan the outside peripheral face of the target 8 (the direction indicated by arrow B), namely, they are provided as ring shapes or annular shapes. Furthermore, the metals 9a and 9b are provided adjacent to one another in a direction perpendicular to the direction in which the electrons scan the outside peripheral face of the target 8 (namely, a direction parallel to the center line X0 in FIG. 2A).

When electrons collide with the first metal 9a, X-rays containing CuKα rays (wavelength 1.542 Å) which are characteristic X-rays is emitted. On the other hand, when electrons collide with the second metal 9b, X-rays containing MoKα rays (wavelength 0.711 Å) which are characteristic X-rays, is radiated. That is, in the present embodiment, the X-ray R1 radiated from the rotor target 8 contains a combination of CuKα rays and MoKα rays, which are characteristic X-rays of the mutually different target materials.

Figure 3A:
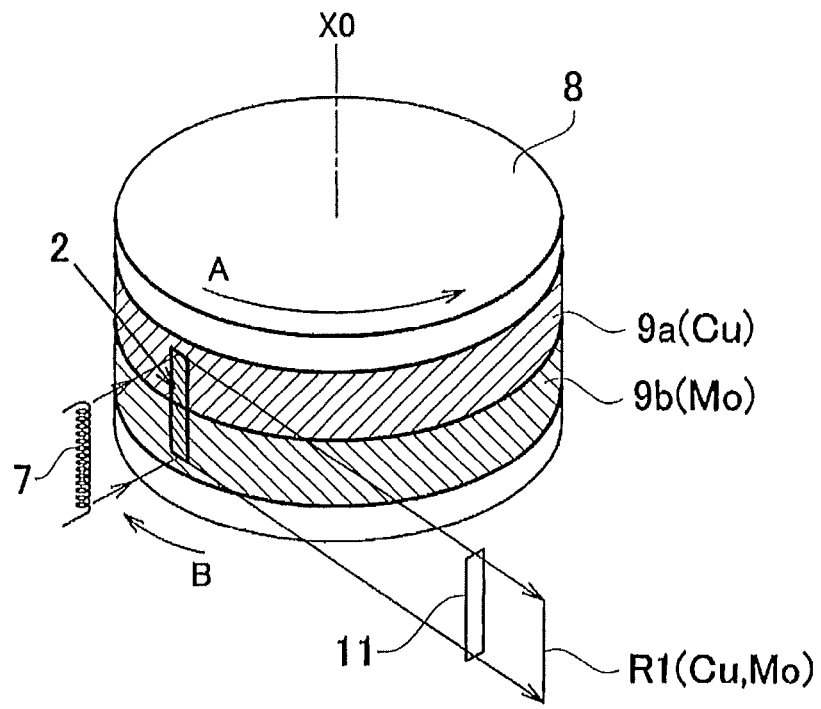
FIG. 3A is a perspective view showing yet another embodiment (line focus) of an X-ray generating section constituting a principal section of the device of FIG. 1.

Depending on the type of sample being measured and the parameters of X-ray measurement, in some cases, instead of a point focus X-ray beam emanating, a line focus X-ray beam like that shown in FIG. 3A will emanate. A line focus X-ray beam refers to an X-ray beam which, of the X-rays radiated from the X-ray focal spot 2, contains X-rays that emanate from a long side of the X-ray focal spot 2, and which has a cross sectional shape of oblong shape elongated in one direction.

Returning to FIG. 1, the sample support device 4 is composed of a simple support stage lacking a moveable member, a three circle goniometer, a four circle goniometer, or the like. A three circle goniometer is a goniometer (namely, an angle measuring instrument) that includes rotation systems rotatable respectively about three rotation axes. A four circle goniometer is an angle measuring instrument that includes rotation systems rotatable respectively about four rotation axes. The decision as to which sample support device structure to use is made depending on the characteristics of the sample 3 and the type of measurement.

The sample 3 is any substance whose molecular structure one wishes to analyze, for example, a single crystal substance, a protein substance, a medicine to be created, or the like. The way in which the sample 3 is supported may be selected appropriately depending on the characteristics of the sample 3. For example, the case of a solid sample such as a single crystal substance, the sample may be affixed to the distal end of a support rod; in the case of a fluid sample, the sample may be placed in a capillary tube; or in the case of a powder sample, the sample may be packed into a recess or through hole of a sample holder. In the case of a protein sample, the sample may be placed in a prescribed storage receptacle. In FIG. 1, the sample 3 is depicted as having spherical shape, but in actual practice, samples of any appropriate shape, depending on the type of sample, may be subjected to measurement.

In the present embodiment, a so-called pulse counting type pixel array two-dimensional detector is used as the X-ray detector 6. This X-ray detector 6 has a planar X-ray detection section 13 constituting the X-ray detecting means, and a signal processing circuit board 14 of about the same surface area as the X-ray detection section 13. The planar type X-ray detection section 13 is formed by arraying two-dimensionally a plurality of X-ray reception pixels 12. In FIG. 1, the individual pixels 12 are depicted larger than actual size in order to aid understanding. The mode of alignment of the plurality of pixels 12 may be selected freely, provided it is a regular alignment.

The signal processing circuit board 14 is provided in contact with or in close proximity to the X-ray detection section 13, at the back face of the X-ray detection section 13 (namely, the opposite face from the receiving surface). As shown in FIG. 4, classification circuits 15 which are individually connected to the plurality of X-ray reception pixels 12, counter sections 16 which are individually connected to the classification circuits 15, a counter readout circuit 17 connected to each of the counter sections 16, and an input/output interface 18 are provided on the signal processing circuit board 14. In FIG. 4, the plurality of pixels 12 are depicted as having a one-dimensional line pattern, but in actual practice, the classification circuits 15 and the counter sections 16 are connected individually to the plurality of pixels 12 disposed in the matrix pattern shown in FIG. 1.

The classification circuits 15 are circuits for classifying the pulse signals of the pixels 12 according to each X-ray wavelength, and outputting the signals. The counter sections 16 are circuits adapted to count the respective numbers of signals that have been classified into every wavelength by the classification circuits 15. The counter sections 16, for example, house counter circuits equal in number to the number of pulse signals classified by the classification circuits 15.

Via the interface 18, the output signal of the counter readout circuit 17 is transmitted through a communication line to an external computer 19, for example, a desktop PC. Alternatively, the output signal of the counter readout circuit 17 may be read out through yet another interface circuit 20, with data processing such as sorting, correction, and the like being carried out by this interface circuit 20. The computer 19 is composed of processing means of known type, for example, a central processing unit (CPU) as operation control means; memory as storage means; system software stored in a prescribed area in memory; application program software stored in another prescribed area in memory, and the like.

A display 21 such as a liquid crystal display device, and a printer 22 such as an electrostatic transfer printing apparatus, are connected to output ports of the computer 19. If needed, the display 21 and the printer 22 can display, on screen or on paper respectively, the results of measurements made according to instructions from the computer 19.

Each of the plurality of pixels 12 is formed by a semiconductor which is predominantly silicon or the like, and upon receiving X-rays, outputs a pulse signal in which a charge generated depending on the wavelength (namely, the energy) of X-rays is represented in terms of integration of the number of X-ray photons. For example, when X ray photons of CuKα rays are received, a peak waveform of wave height V1 is output, whereas when X-ray photons of MoKα rays are received, a peak waveform of wave height V2 is output. Because CuKα<MoKα is satisfied with regard to the energy of the X-ray photons, V1<V2 is satisfied.

The classification circuits 15 are circuits adapted to classify the output signals of the pixels 12 in terms of every wavelength, which signals are output in different states (in the present embodiment, as different peak height values) for every wavelength (namely, for every energy level); and to then output the signals. As shown for example in FIG. 5, the classification circuit 15 has a signal amplification amp 23, a waveform shaping circuit 24 for shaping the peak waveform to a peak waveform appropriate for a counter, and two comparators 26a, 26b. Voltages Va and Vb are respectively applied to the standard reference voltage terminal of each of the comparators 26a, 26b.

V1<Va<V2, and Vb<V1. Consequently, the comparator 26a outputs an output signal of wave height V2 (corresponding to MoKα rays) which is greater than Va. On the other hand, the comparator 26b outputs both the wave heights V1 (corresponding to CuKα rays) and V2 (corresponding to MoKα rays), which are greater than Vb.

Figure 5:
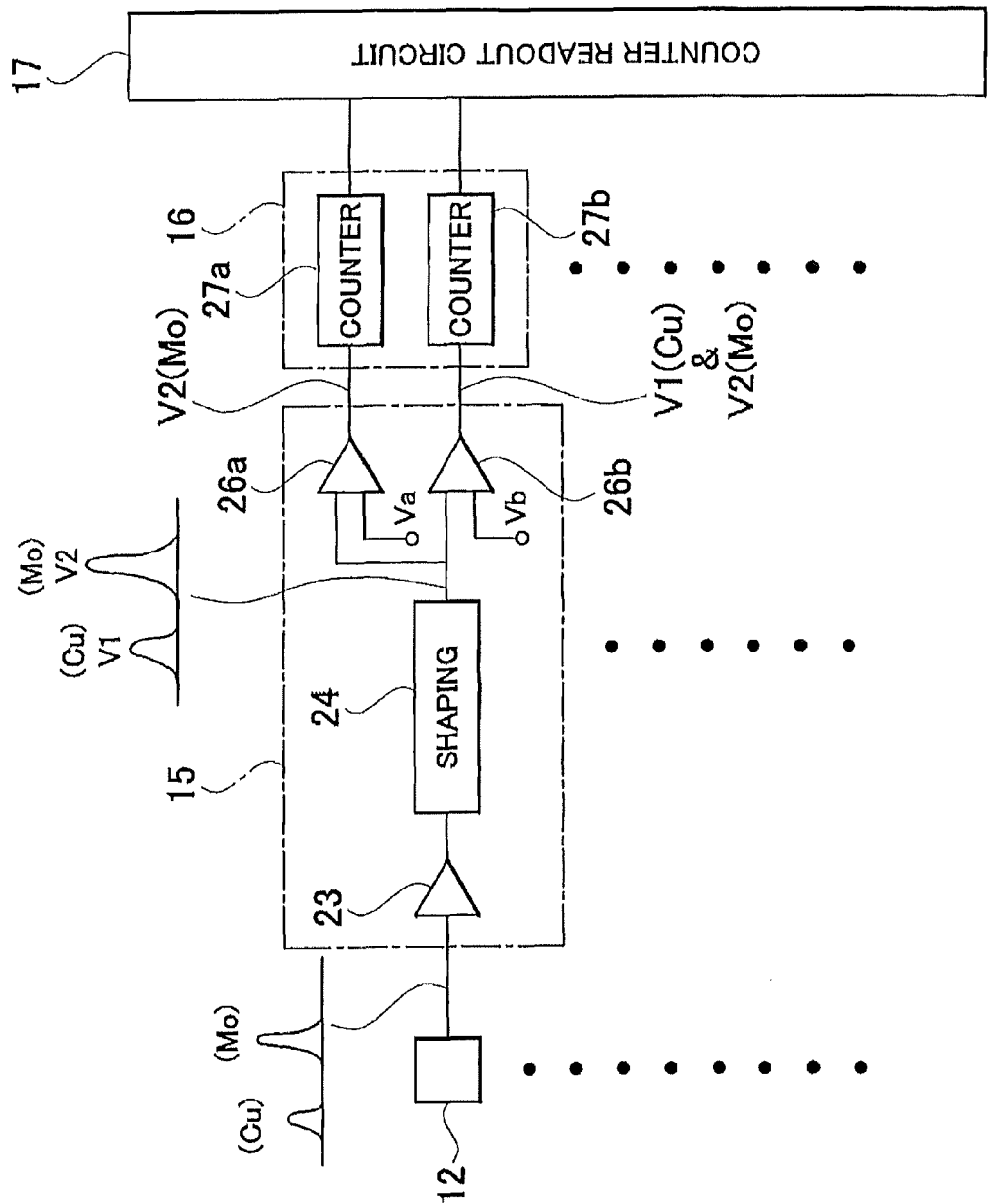
FIG. 5 is a block diagram showing an embodiment of internal circuitry of the principal section of the block diagram of FIG. 4.

As shown in FIG. 5, the counter section 16 of FIG. 4 has counters 27a and 27b which are connected to individual output terminals of the comparators 26a, 26b. Each time that a signal is output to an output terminal of the comparators 26a, 26b, the counters 27a, 27b count the output signal, and output the count number observed within a prescribed time interval as an output signal. The counter 27a outputs the count number of the wave height V2, while the counter 27b outputs a count number obtained by addition of the count number of the wave height V1 and the count number of the wave height V2.

The counter readout circuit 17 determines the count number of the wave height V2 from the count number of the counter 27a, and calculates the count number of the wave height V1 from a value obtained by subtraction of the count number of the counter 27a (namely, the count number of the wave height V2) from the count number of the counter 27b (namely, the count number of the wave height V1+the count number of the wave height V2). The counter readout circuit 17 then outputs how many pulses of wave height V1 (corresponding to CuKα rays) were counted and how many pulses of wave height V2 (corresponding to MoKα rays) were counted, in a pixels 12 at a row/column address (i,j). In FIG. 4, this output signal is transmitted to the computer 19.

On the basis of in-plane positions of diffracted X-rays which have been detected by the planar X-ray detection section 13 shown in FIG. 1, and of intensity count values for every wavelength of diffracted X-rays which have been calculated by the counter readout circuit 17, the computer 19 computes relationships among diffracted X-ray wavelengths, diffraction angles of diffracted X-rays, and intensity of diffracted X-rays. Namely, for X-rays of specific wavelength, the computer 19 computes the diffraction angle of diffracted X-rays and the intensity count of diffracted X-rays. By doing this, diffractograms representing relationships of diffraction angle and diffraction intensity, namely, diffraction profiles, of diffracted X-rays can be acquired on a per-wavelength basis, and can also be displayed on a screen or the like.

Because the wavelength-classifying type X-ray diffraction device 1 according to the present embodiment is configured as above, in FIG. 1, a point focus X-ray R1 (see FIG. 2A) containing CuKα rays and MoKα rays from the X-ray focal spot 2 which is the X-ray source, or in some cases a line focus X-ray R1 (see FIG. 3A) if needed, is radiated, and the X-ray impinges on the sample 3. If the sample 3 has a crystal lattice plane matching CuKα rays, a diffracted X-ray R2 of CuKα rays is output from the sample, or if the sample 3 has a crystal lattice plane matching MoKα rays, a diffracted X-ray R3 of MoKα rays is output from the sample.

The diffracted X-ray R2 of CuKα rays and the diffracted X-ray R3 of MoKα rays are received simultaneously (namely, when the sample 3 is bombarded with X-rays one time) within the entire region of the receiving surface of the two-dimensional X-ray detection section 13. At this time, an image of the diffracted X-ray R2 and an image of the diffracted X-ray R3 are classified individually in the plurality of pixels 12 by the classification circuits 15 of FIG. 4, and the images so classified are counted in terms of every wavelength and in terms of every one of the individual pixels, by the counter sections 16.

The intensity of diffracted X-rays of every wavelength are derived as count numbers by the counter readout circuit 17, and the results are transmitted in the form of an electrical signal to the computer 19. According to control by program software installed therein, the computer 19 determines diffracted X-ray intensities of every wavelength in association with addresses (i, j) of the pixels 12, and saves the resultant data to a prescribed area in memory in the computer 19.

Figure 6:
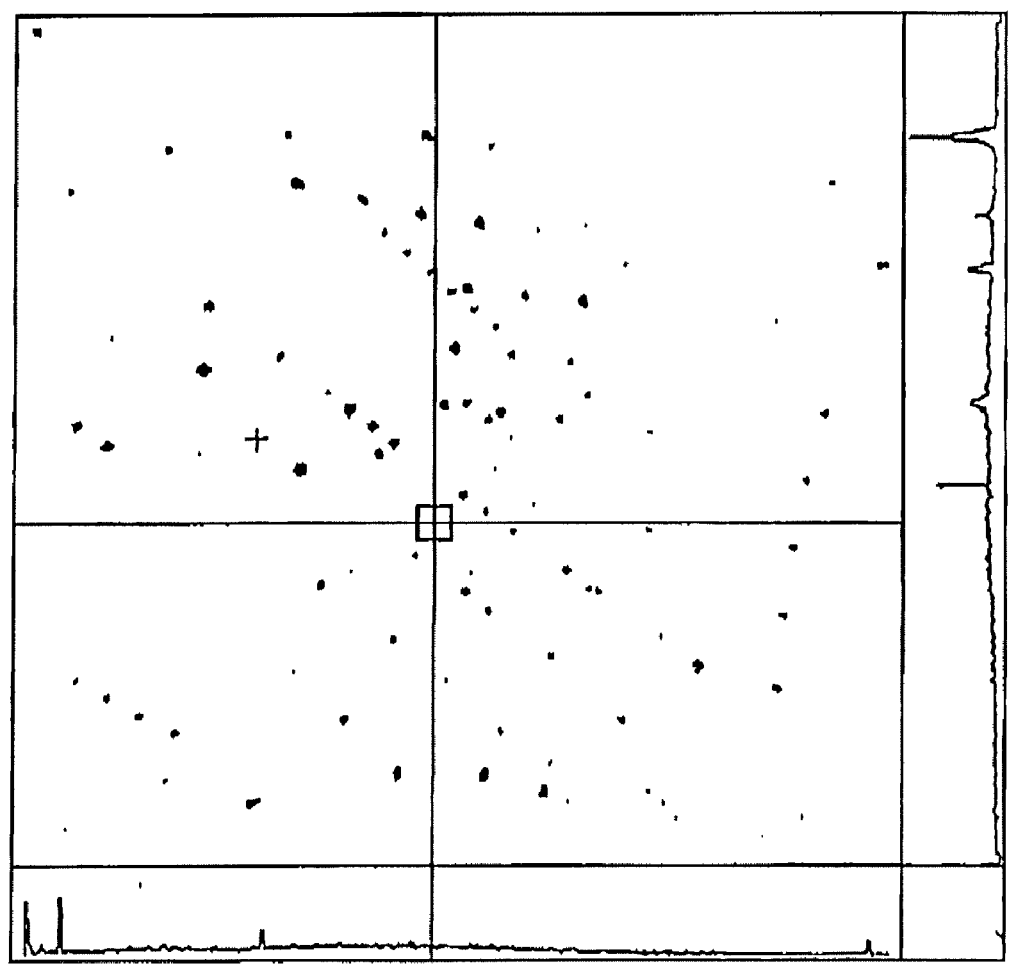
FIG. 6 is a diagram showing an example of a diffracted X-ray image obtained as a measurement result.

If the data of diffraction images of both the image of the diffracted X-ray R2 (namely, Cu image) and the image of the diffracted X-ray R3 (namely, Mo image) which have been saved to memory is displayed by the display 21 or the printer 22 according to a prescribed image display program, there will be displayed a two-dimensional diffraction image in which both the diffracted X-ray R2 (Cu image) and the diffraction image of the diffracted X-ray R3 (Mo image) are widely distributed in combination, as shown, for example, in FIG. 6.

Figure 7:
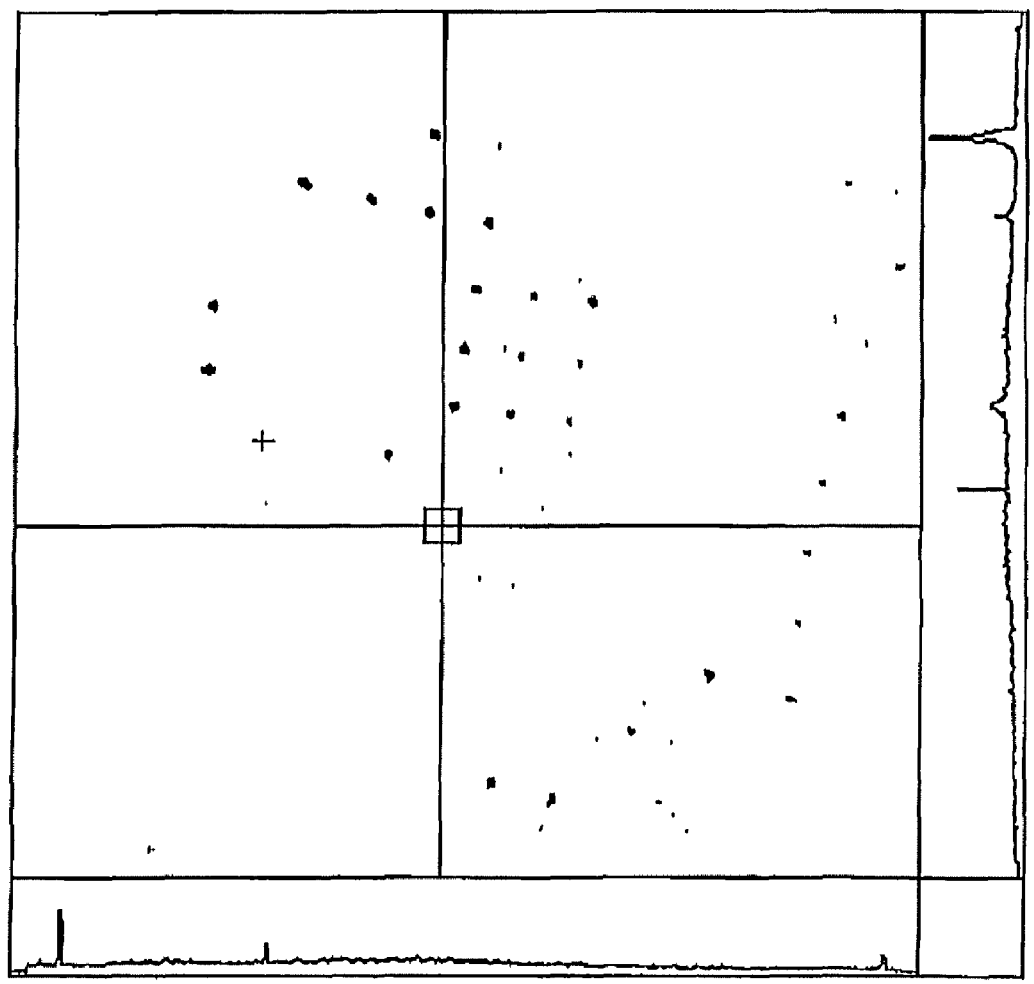
FIG. 7 is a diagram showing a diffracted X-ray image obtained from the measurement data of FIG. 6 by compiling and discrimination with Cu only.

Meanwhile, if according to a prescribed wavelength selection program, the image of the diffracted X-ray R2 (Cu image) is selected from the diffraction image data of both the image of the diffracted X-ray R2 (Cu image) and the image of the diffracted X-ray R3 (Mo image) which have been saved to memory, and this selected data is displayed on the display 21 or the like, only the image of the diffracted X-ray R2 (Cu image) is selectively displayed and can be observed, as shown in FIG. 7.

Figure 8:
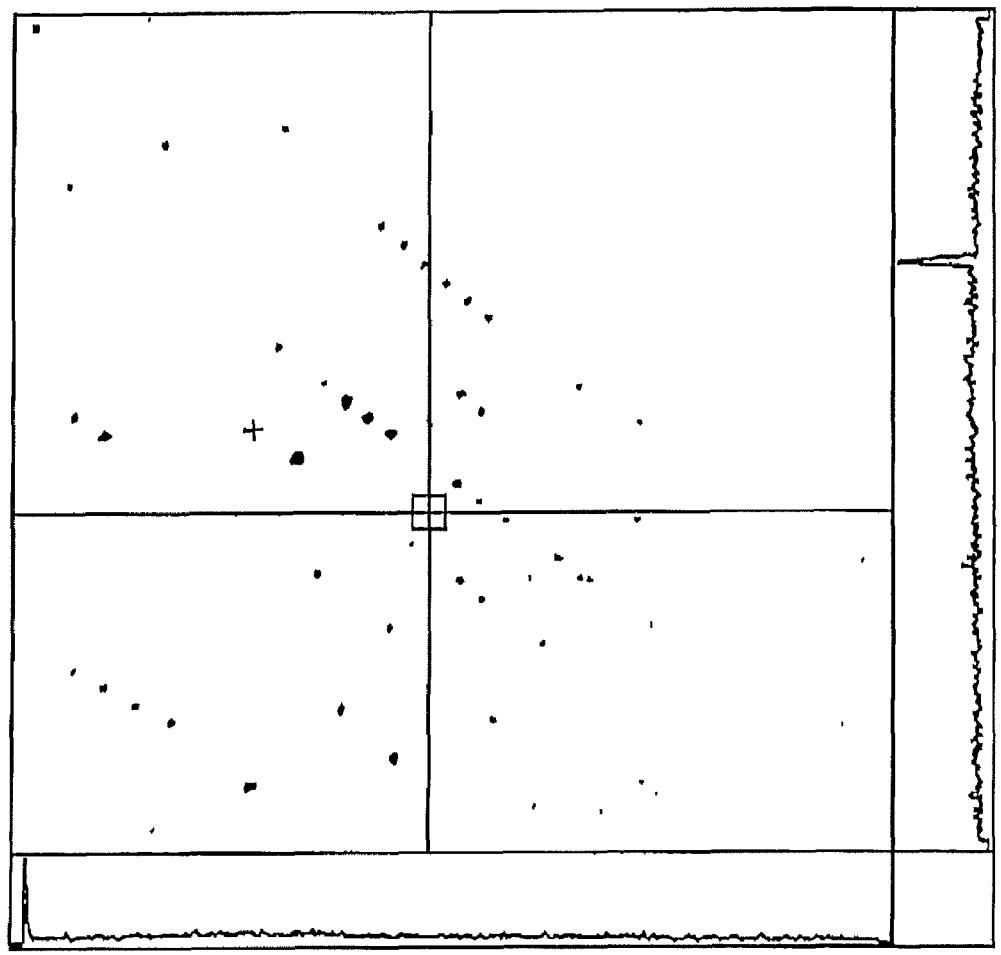
FIG. 8 is a diagram showing a diffracted X-ray image obtained from the measurement data of FIG. 6 by other compiling and discrimination with Mo only.

On the other hand, if according to a prescribed wavelength selection program, the image of the diffracted X-ray R3 (Mo image) is selected from the diffraction image data of both the image of the diffracted X-ray R2 (Cu image) and the image of the diffracted X-ray R3 (Mo image) which have been saved to memory, and this selected data is displayed on the display 21 or the like, only the image of the diffracted X-ray R3 (Mo image) is selectively displayed and can be observed, as shown in FIG. 8.

In the above manner, according to the wavelength-classifying type X-ray diffraction device 1 of the present embodiment, a diffracted X-ray beam containing diffracted X-rays of different wavelengths (e.g., CuKα rays and MoKα rays) is detected by the pixel array detector 6 in which every pixel 12 is given wavelength classifying functionality, and therefore diffracted X-rays of every wavelength can be detected. Because of this, measurement data based on X-rays of different wavelengths can be acquired simultaneously by measurement just one time. In so doing, waste of energy in the X-ray generation section shown in FIG. 2A can be prevented, wear of the target 8 within a short time can be prevented, and measurement data based respectively on X-rays of different wavelengths can be acquired in a short period of time. Because measurements are completed within a short period of time, measurements can be carried out without problems even on a sample 3 (FIG. 1) which is unable to maintain crystal structure for extended periods.

In certain conventional X-ray diffraction devices, the planar X-ray detection section that makes up the X-ray detector is not formed by a pulse counting type pixel array detector, but rather by a charge integrating type CCD detector, and the receiving surface of the X-ray detection section is divided into upper and lower halves or the like, with diffracted X-rays of different wavelengths being received by the respective divided regions. With this structure, the detection region for each wavelength is constricted, and there is a risk of diminished reliability of data. With the X-ray diffraction device of the present embodiment, by contrast, diffracted X-rays of different wavelengths are respectively received over the entire region of the receiving surface of the X-ray detection section 13 of the X-ray detector 6, and therefore data of a plurality of diffracted X-rays of different wavelengths can be respectively acquired over a wider range, and highly reliable diffracted X-ray data can be obtained as a result.

Second Embodiment

The present embodiment is similar to the first embodiment, but with a modification made to the X-ray generation section.

As shown in FIG. 2A and FIG. 3A, in the first embodiment described above, the first metal 9a and the second metal 9b are respectively continuous along the direction in which electrons from the filament 7 scan the outside peripheral face of the target 8 (the direction indicated by arrow B), namely, they are provided as ring shapes or annular shapes. Furthermore, the first metal 9a and the second metal 9b are provided adjacent to one another along a direction perpendicular to the direction in which electrons scan the outside peripheral face of the target 8 (a direction parallel to the center line X0 in FIG. 2A).

Figure 2B:
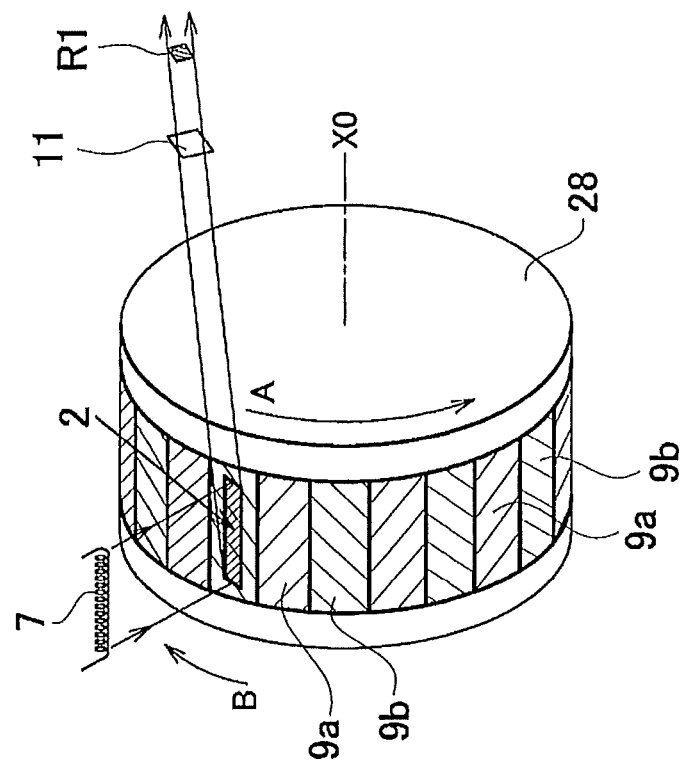
FIG. 2B is a perspective view showing another embodiment (point focus) of the X-ray generating section.
Figure 3B:
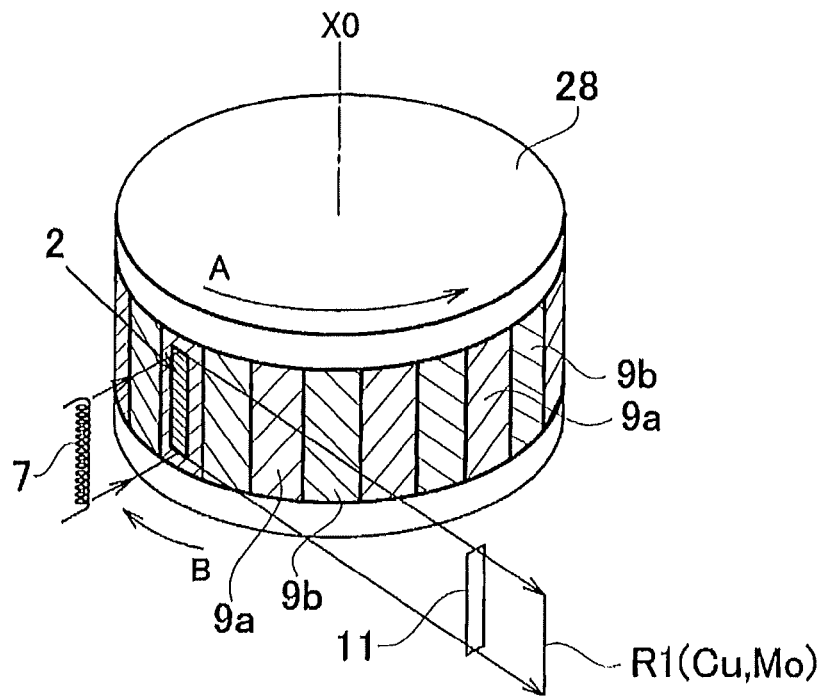
FIG. 3B is a perspective view showing yet another embodiment (line focus) of the X-ray generating section.

By contrast, in the present embodiment, the first metal 9a and the second metal 9b are provided in alternating prescribed widths along the direction in which electrons from the filament 7 scan the outside peripheral face of a target 28 (the direction indicated by arrow B) as shown in FIG. 2B and FIG. 3B. In this structure, the metal 9a and the metal 9b are provided in a striped pattern, namely, in a stripe pattern, and it is therefore sometimes referred to as a stripe type target. The structure is also called a zebra type target. FIG. 2B is a structure for the purpose of emanating a point focus X-ray beam, and FIG. 3B is a structure for the purpose of emanating a line focus X-ray beam.

According to the present embodiment as well, by emission of electrons from the filament 7 and rotation of the target 28 about its center axis X0, the X-ray R1 emitted from the X-ray focal spot 2 can contain X-rays of different wavelengths. That is, according to the present embodiment, the X-ray R1 emitted from the rotor target 28 contains a combination of characteristic X-rays of the mutually different target materials, i.e., CuKα rays and MoKα rays.

Modified Examples

The first metal 9a shown in FIGS. 2A, 2B, 3A, and 3B is not limited to Cu. Likewise, the second metal 9b is not limited to Mo. The X-rays of R1, R2, and R3 shown in FIG. 1 are not limited to Cu rays and Mo rays. In FIG. 5, the two comparators 26a, 26b, the counters 27a, 27b, and the counter readout circuit 17 utilize subtraction to classify two wavelengths, i.e., the wavelength indicated by the pulse height V1 and the wavelength indicated by the pulse height V2. However, by instead establishing three or more standard reference voltages, namely, threshold values, the wavelength indicated by the pulse height V1 and the wavelength indicated by the pulse height V2 may be classified directly, without performing a subtraction operation.

Further, whereas in the embodiment described above, the targets 8, 28 in FIGS. 2A, 2B, 3A, and 3B are provided with two metals 9a, 9b, optionally, the target surfaces may instead be provided with three or more metals, and X-rays of three or more wavelengths generated. In this case, the numbers of the comparators 26a, 26b and the counters 27a, 27b of FIG. 5 will increase as needed.

Third Embodiment

Figure 9:
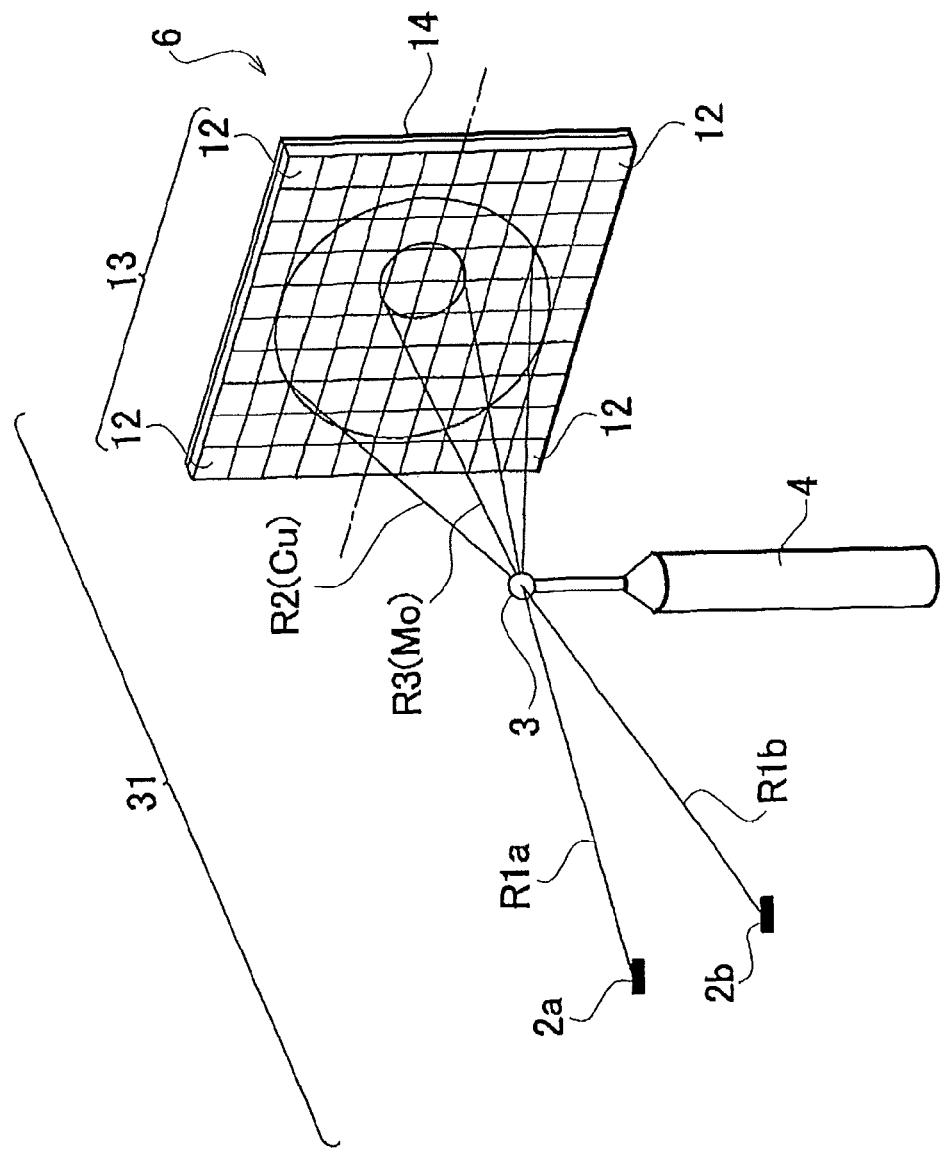
FIG. 9 is a perspective view showing another embodiment of the wavelength-classifying type X-ray diffraction device according to the present invention.

FIG. 9 shows another embodiment of the wavelength-classifying type X-ray diffraction device according to the present invention. The present embodiment is likewise similar to the first embodiment, but with a modification to the X-ray generation section. In the first embodiment described previously, an X-ray R1 containing a plurality of characteristic X-rays of different wavelengths emitted from a single X-ray source, namely, the X-ray focal spot 2, as shown in FIG. 1.

By contrast, according to the present embodiment shown in FIG. 9, an X-ray R1a radiated from a first X-ray source 2a constituting a first X-ray generation section and an X-ray R1b radiated from a second X-ray source 2b constituting a second X-ray generation section simultaneously bombard the sample 3. The X-ray R1a and the X-ray R1b are both X-rays of a single wavelength. In this embodiment, the incident angles of the X-ray R1a and the X-ray R1b onto the sample 3 differ. The structure is otherwise the same as the X-ray diffraction device 1 shown in FIG. 1. Here, the X-rays of R1a, R1b, and R3 are not limited to Cu rays and Mo rays.

Fourth Embodiment

Following is a description of an embodiment in a case where the present invention is implemented in structure analysis of a sample having small molecular mass, containing a heavy atom. The overall structure of the wavelength-classifying type X-ray diffraction device of the present embodiment can be the structure shown in FIG. 1 or FIG. 9. In the case of FIG. 1, characteristic X-rays arising from the mutually different target materials, namely, CuKα rays and MoKα rays, are emitted simultaneously from the X-ray focal spot 2 and are supplied to the sample 3. The X-rays supplied to the sample are point focus (see FIGS. 2A, 2B), for example.

The heavy atoms mentioned above are Fe, Co, Mo, and W for example. Light atoms, on the other hand, are C, H, N, O, and S, for example. Typically, CuKα rays (wavelength 1.542 Å) is readily absorbed by heavy atoms, whereas MoKα rays (wavelength 0.711 Å) is absorbed with difficulty by heavy atoms. Consequently, in most instances, MoKα rays is used in structure analysis of samples having small molecular mass.

However, because CuKα rays has higher X-ray efficiency, there is the advantage that a high intensity X-ray can be supplied to a small crystal. Also, because samples of long lattice length have narrow spacing between diffraction images of point form, it is difficult to carry out observation of diffraction images. Meanwhile, because CuKα rays have a long wavelength, there is wide spacing between diffraction images, and a resultant advantage is that it is easy to carry out observation of diffraction images. Owing to the advantages mentioned above, in cases of small crystal size or long lattice length, it is desirable to use Cu rays, even if heavy atoms are contained.

Consequently, for samples of long lattice length containing heavy atoms and having small crystal size, there is sometimes a need to determine the initial structure using Cu rays, and to carry out refining of the structure using Mo rays. The wavelength-classifying type X-ray diffraction device of the present embodiment is adapted to meet this need. According to the wavelength-classifying type X-ray diffraction device of the present embodiment, data by Cu rays and data by Mo rays can be acquired simultaneously in a single process (namely, X-ray bombardment of a sample just one time).

The planar size of the two-dimensional pixel array detector is from 60 mm×80 mm to 120 mm×160 mm, for example. There are no specific limitations as to the size and number of individual pixels forming the pixel array detector. However, pixel size is preferably a size such that resolution of at least 0.1° can be attained. Once the planar size of the detector and the pixel size have been determined, the number of pixels is determined automatically.

Fifth Embodiment

In the field of analyzing crystal structure, optical isomers, namely, chirality, are known. The wavelength-classifying type X-ray diffraction device of the present embodiment may be used for structure analysis of substances having optical activity. The overall structure of the wavelength-classifying type X-ray diffraction device of the present embodiment can be the structure shown in FIG. 1 or FIG. 9. In the case of FIG. 1, characteristic X-rays arising from the mutually different target materials, namely, Cu rays and Mo rays, are emitted simultaneously from the X-ray focal spot 2 and are supplied to the sample 3. The X-rays supplied to the sample are point focus (see FIGS. 2A, 2B), for example.

Figure 10A:
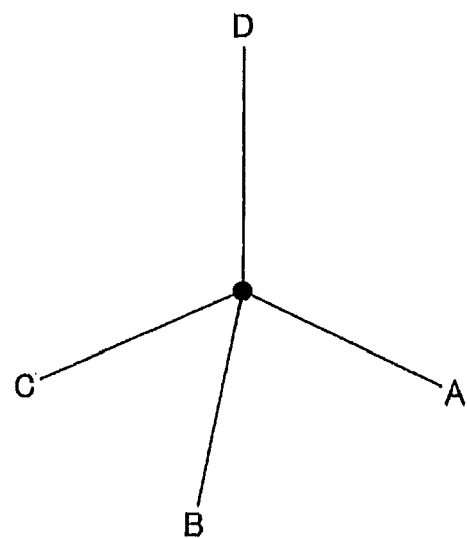
FIG. 10A and FIG. 10B are respectively diagrams illustrating yet another embodiment of the wavelength-classifying type X-ray diffraction device according to the present invention.
Figure 10B:
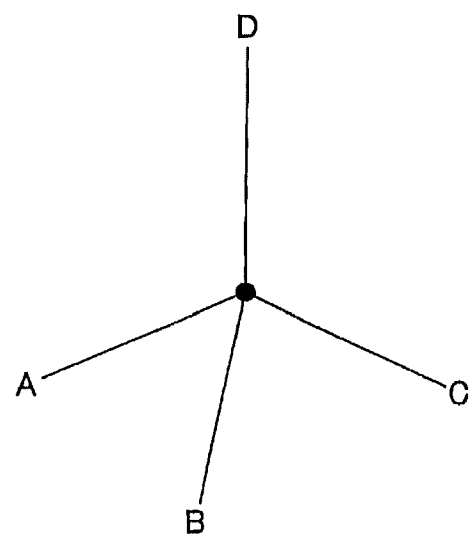

As depicted generically in FIGS. 10A and 10B, optical isomers are substances that, despite having the same chemical structural formula, exhibit different behavior stemming from differences in steric structure. For example, the R-configuration of FIG. 10A is useful as a drug, whereas the S-configuration of FIG. 10B exhibits toxicity. Ordinarily, diffracted X-rays of two optical isomers are substantially equivalent, but slight differences arise in relation to a portion of anomalous scattering, namely, a portion of abnormal dispersion; and slight discrepancies between the two in terms of diffracted X-ray intensity are observed.

When deriving which structure is present by detecting such slight discrepancies, namely, when deriving absolute structure, the Flack parameter provides an indicator.

However, in the case of organic compounds composed exclusively of light atoms such as C (carbon), H (hydrogen), N (nitrogen), and O (oxygen), these slight differences cannot be detected unless X-rays of particularly long wavelength are used, and structural determination using the Flack parameter is difficult. Consequently, in structure analysis of optical isomers, there is sometimes a need to derive the Flack parameter using CuKα rays, and to then carry out refining of structure using MoKα rays. The wavelength-classifying type X-ray diffraction device of the present embodiment is adapted to meet this need.

According to the wavelength-classifying type X-ray diffraction device of the present embodiment, data by Cu rays and data by Mo rays can be acquired simultaneously in a single process (namely, X-ray bombardment of a sample just one time).

Sixth Embodiment

Following is a description of an embodiment in a case of implementation of the invention in structure analysis of protein crystals. The overall structure of the wavelength-classifying type X-ray diffraction device of the present embodiment can be the structure shown in FIG. 1 or FIG. 9. In the case of FIG. 1, a plurality of characteristic X-rays based on mutually different target materials are emitted simultaneously from the X-ray focal spot 2 and are supplied to the sample 3. The X-rays supplied to the sample are point focus (see FIGS. 2A, 2B), for example.

As is well known, proteins are amino acid substances formed of light atoms, such as C (carbon), N (nitrogen), etc. Analysis of crystal structure using X-rays is a favorable method for determining steric structure of proteins on an atomic level. Specifically, the positions of atoms can be determined through calculations from the intensity distribution of scattered rays leaving the protein crystal. More specifically, structure analysis using X-rays involves subjecting a structure factor F (hkl) to Fourier transformation to derive electron density $\rho$ (xyz).

Figure 11:
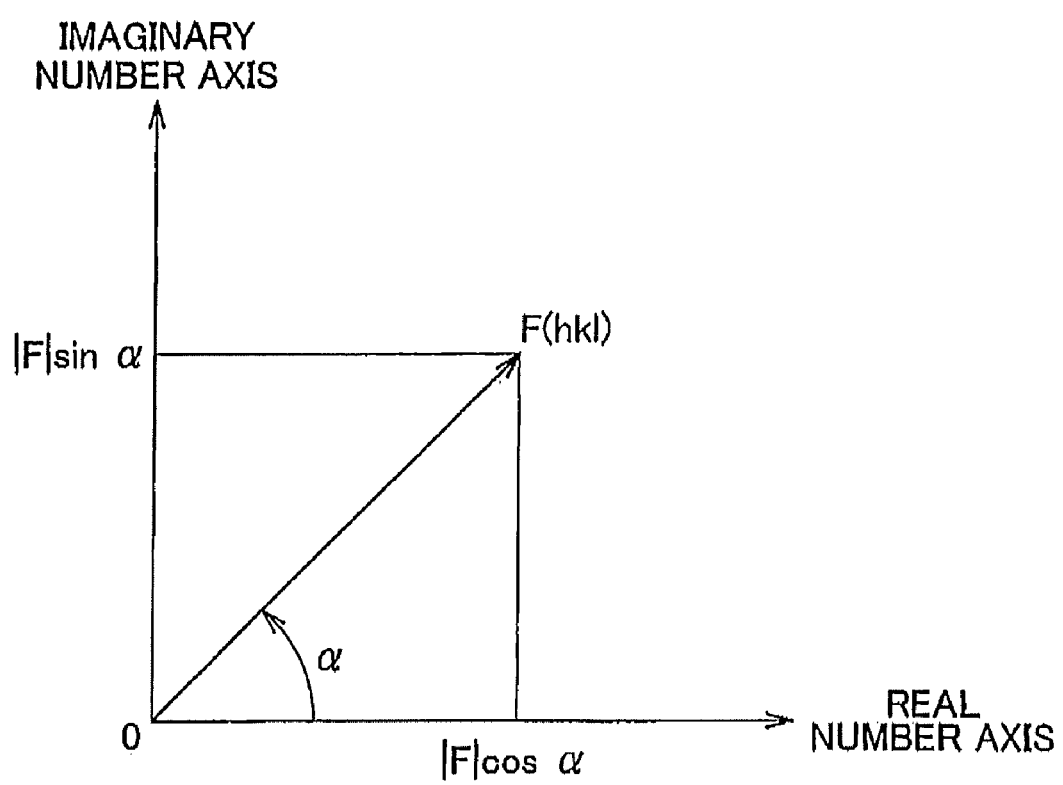
FIG. 11 is a diagram illustrating yet another embodiment of the wavelength-classifying type X-ray diffraction device according to the present invention.

As shown in FIG. 11, the structure factor F (hkl) is a complex quantity, and the complex quantity F (hkl) cannot be specified unless |F (hkl)| (absolute value) and phase angle $\alpha$ are known. The absolute value |F (hkl)| of the structure factor is obtained by measuring diffracted X-ray intensity I(=|F (hkl)|$^2$). The phase angle $\alpha$ cannot be derived empirically. There are any of a number of known conventional methods which may be used as the method for determining phase angle $\alpha$. One known method among these is the multi-wavelength anomalous dispersion (MAD) method. In recent years, the single-wavelength anomalous dispersion (SAD) method has come to be used as well.

MAD method is a method of utilizing the effect of anomalous scattering in the vicinity of the absorption edge of a specific atom contained in a protein, in order to determine phase. Specifically, diffracted X-ray intensity is measured using X-rays of at least three different wavelengths which bracket the absorption edge of a specific atom. SAD method is a method of determining phase exclusively from the intensity of X-rays scattered anomalously, as measured with an X-ray of a single given wavelength.

In the present embodiment, where the phase angle $\alpha$ of the structure factor F (hkl) is to be derived by the MAD method, using three kinds of X-rays selected from CuKα rays (wavelength 1.542 Å), CoKα rays (wavelength 1.789 Å), CrKα rays (wavelength 2.290 Å) and MoKα (wavelength 0.711 Å), the diffraction angle and diffracted X-ray intensity are measured on the basis of each X-ray. In this case, the electron receiving surface (namely, the X-ray emitting surface) is formed by providing the metals Cu, Co, Cr and Mo to the surface of the rotor target that makes up the X-ray generation device.

In the present embodiment, where SAD method is implemented, phase angle is determined using either CrKα rays or CoKα rays, and then refining of measurement of diffracted X-ray intensity is carried out using CuKα rays. Because both CrKα rays and CoKα rays experience high absorption by the sample, it is suitable for determining phase angle. Because CuKα rays experiences low absorption by the sample and diffracted X-ray intensity of CuKα rays is strong, good diffraction data can be obtained, and refined analysis can be carried out.

Proteins are substances of long lattice length. Specifically, lattice length ranges from 100 to 500 Å. If lattice length is long, the diffraction images of point form obtained therefrom will be represented by a narrow scale (namely, a narrow scale of diffracted angle), making observation difficult. In this case, by using Cu rays, which has longer wavelength than Mo rays, the scale for representing diffracted images is wider, and it is possible for observation of the diffraction profile to be carried out easily.

According to the present embodiment, both in the case of the MAD method and in the case of the SAD method, X-rays of a plurality of wavelengths bombard a single protein sample, and diffracted X-rays corresponding to those wavelengths are received simultaneously by a two-dimensional pixel array detector. The two-dimensional pixel array detector then detects the diffraction angles and the diffracted X-ray intensities in relation to the received diffracted X-rays, on a per-wavelength (i.e. a per-energy level) basis.

The planar size of the two-dimensional pixel array detector is from 80 mm×120 mm to 240 mm×240 mm, for example. There are no specific limitations as to the size and number of individual pixels forming the pixel array detector. However, the pixels are preferably of such size that resolution of at least 0.1° can be attained. Once the planar size of the detector and the pixel size have been determined, the number of pixels is determined automatically.

Seventh Embodiment

Following is a description of an embodiment in a case of implementation of the invention in structure analysis of powder samples. The overall structure of the wavelength-classifying type X-ray diffraction device of the present embodiment can be the structure shown in FIG. 1 or FIG. 9. In the case of FIG. 1, a plurality of characteristic X-rays based on mutually different target materials are emitted simultaneously from the X-ray focal spot 2 and bombard the sample 3. The X-rays bombarding the sample are line focus (see FIGS. 3A, 3B), for example.

Figure 12A:
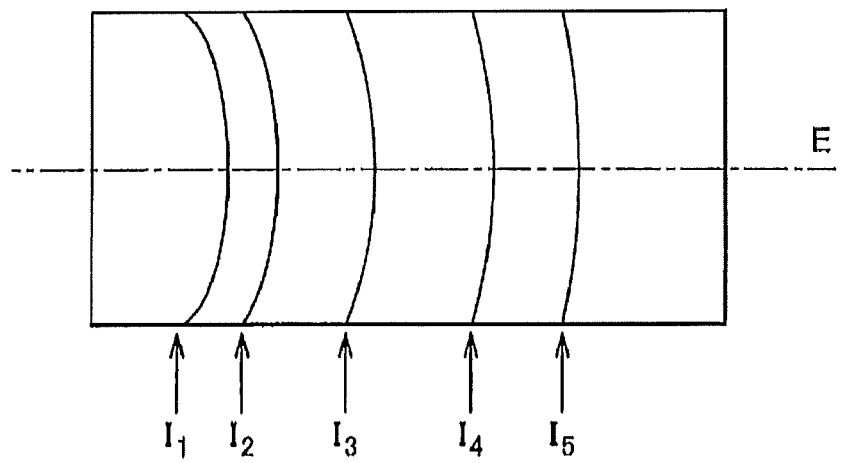
FIG. 12A and FIG. 12B are respectively diagrams illustrating yet another embodiment of the wavelength-classifying type X-ray diffraction device according to the present invention.
Figure 12B:
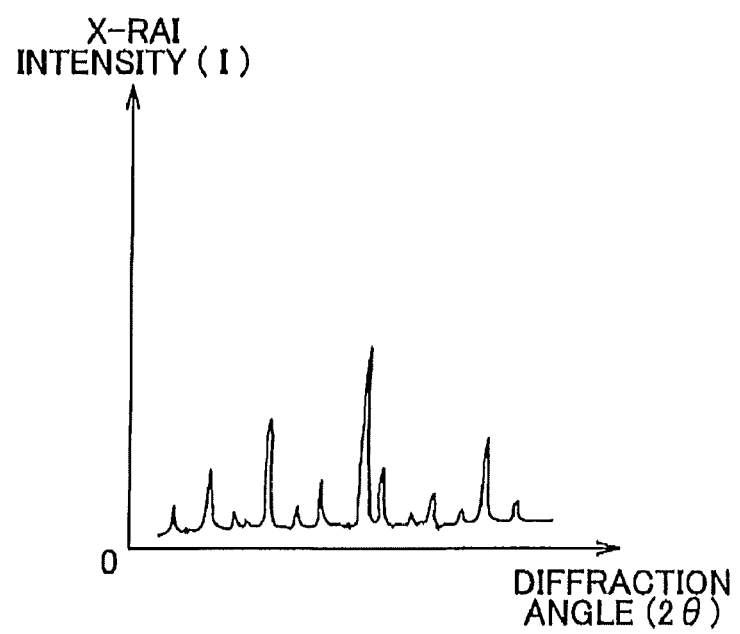

As shown in FIG. 12A, in analysis of a powder sample, in typical practice two-dimensional diffraction images $I_1$, $I_2$, $I_3$ . . . are derived through measurements, the diffraction images are individually integrated, and diffracted X-ray intensities at individual angles of diffraction angle 2θ are identified. The diffraction images are then displayed as a diffraction profile on the diffractogram of FIG. 12B, whose horizontal axis is an axis corresponding to the equatorial line E.

Because the diffraction angle becomes progressively smaller at shorter wavelengths of the X-rays used for measurements, the scale for representing diffraction images (the so-called diffracted X-rays) on the axis of the diffractogram is a narrow representation. On the other hand, because the diffraction angle becomes progressively larger at longer wavelengths of the X-rays used for measurements, the scale for representing diffraction images (so-called diffracted X-rays) on the axis of the diffractogram is a wide representation.

Thus, when X-rays used for measurement have a long wavelength, the diffraction profile thereof is easily observed once analysis has been implemented in relation to the diffraction profile of diffraction images (so-called diffracted X-rays). Consequently, in normal powder measurement, apart from special circumstances there are few instances in which short-wavelength X-rays are used. For example, CuKα rays, which has a wavelength of 1.5418 Å, has a longer wavelength than MoKα rays, which has a wavelength of 0.7107 Å, and is the X-ray most widely used for powder measurement.

However, for substances that belong to the class of metals, CuKα rays typically experiences an especially high proportion of absorption as compared with MoKα rays, and for this reason there arises the problem of lack of distinctness of two-dimensional diffraction images derived using CuKα rays, owing to the effects of scattered X-rays caused by this absorption; and specifically, a problem of insufficient characteristics of distinctly representing diffraction images (so-called diffracted X-rays) on two-dimensional images. Also, in measurements in which X-rays transmit (namely, pass through) a sample, in cases where the sample contains heavy atoms, there is the problem that, with CuKα rays, transmission is difficult due to high absorption. Because MoKα rays has a short wavelength, the scale for representation in the diffraction angle direction (typically the horizontal axis direction) of diffraction images (so-called diffracted X-rays) obtained on a diffractogram represented by coordinates narrows; and in the case, for example, of a sample of large crystal structure, such as a mineral or polymer, adjacent diffraction images (so-called diffracted X-rays) may overlap, making it difficult to determine the index of lattice plane (hkl) representing the diffraction images (so-called diffracted X-rays).

In view of the above problem, in the present embodiment, the surface of the rotor target that makes up the X-ray generation device is provided with metals Cu and Mo which are metals of mutually different atomic numbers, in order to form the electron receiving surface (namely, the X-ray emitting surface). Two types of X-rays, CuKα rays and MoKα rays, are emitted simultaneously from the X-ray focal spot within the electron receiving surface, namely, the X-ray source, and simultaneously bombard the powder sample.

Then, based on a diffraction profile obtained with CuKα rays, the crystal system and the lattice constant are determined from the index of lattice plane (hkl). Simultaneously, refining of crystal structure is carried out on the basis of diffraction images obtained with MoKα rays. Specifically, the number of atoms per unit lattice and the positions of the atoms are clearly identified.

In the case of the powder sample described above, because two-dimensional data is converted to one-dimensional data on the equatorial line, the detector may be considered as fundamentally one-dimensional (namely, linear) rather than two-dimensional (namely, planar). While certainly this may be said to be the case, an advantage of using a two-dimensional pixel array detector is that in cases where there is a preferred orientation of the powder sample, the effect of non-uniformity of diffraction intensity arising from this orientation can be better ameliorated, as compared with the case of the one-dimensional pixel array detector.

The planar size of the two-dimensional pixel array detector is 30 mm×80 mm, for example. There are no specific limitations as to the size and number of individual pixels forming the pixel array detector. However, pixels are preferably of such size that resolution of 0.01° on a diffraction profile of diffraction images (so-called diffracted X-rays) can be attained. Once the planar size of the detector and the pixel size have been determined, the pixel count is determined automatically. In the case measurement data of a wide 2θ angle range is desired, the planar size of the detector can be made larger; or a method of scanning with a detector of small planar size can be adopted.

Another Embodiment

While the present invention was shown hereinabove in terms of certain preferred embodiments, the invention is not limited to these embodiments; various modifications are possible within the scope of the invention recited in the claims.

For example, in the embodiment shown in FIG. 1, the signal processing circuit board 14 is provided in contact with or in close proximity to the back face of the X-ray detection section 13 which is composed of a plurality of pixels 12 aligned two-dimensionally, namely, in planar fashion. However, the X-ray detection section 13 and the signal processing circuit board 14 could instead be positionally separated, and connected to the individual pixels 12 and the processing circuits by appropriate connection lines.

In the preceding embodiments, different metals are provided through a method such as adhesion to different positions on the surface of the target, but instead, a structure whereby the target surface is formed of an alloy that is a combination of different metals can be adopted.

In the preceding embodiments, as shown in FIG. 5, the threshold values Va and Vb are set such that $$Vb<V1<Va<V2$$

where V1 is a potential corresponding to CuKα rays and V2 is a potential corresponding to MoKα rays. That is, the Mo wavelength and the Cu wavelength are classified by Va and Vb. However, a classification method such as the following can be adopted instead.

In a case where, for example, MoKα rays and CuKα rays are used for the purpose of measurement, Mo and Cu are used as the different metals forming the target. In this case, Mo and Cu also generate characteristic X-rays besides Kα rays, for example, Kβ rays, Lα rays, Lβ rays, and the like. These characteristic X-rays besides Kα act as noise for the purposes of measurement. Where highly accurate measurements are desired, it is preferable to elicit only energy corresponding to Kα rays, while eliminating other noise components. Through finer setting of threshold values in place of the threshold values Va and Vb described above so as to be able to shave the upper and lower regions of a desired wavelength, excess noise components in X-rays can be excluded, and measurements can be carried out with high accuracy.

In the preceding embodiments, the anti-cathode which is a constituent element of the X-ray source is a rotor target, namely, a rotating anti-cathode; however, it could instead be a fixed target, namely, a non-rotating anti-cathode. As techniques for simultaneously obtaining different characteristic X-rays from a fixed target, there may be contemplated, for example, a technique in which the fixed target is formed of an alloy; or in which very small areas of different metals combine, for example, combine in a dappled manner, on the surface of the fixed target, and so on.

What is claimed is:

1. A wavelength-classifying type X-ray diffraction device for bombarding a sample with characteristic X-rays generated by X-ray generating means, and detecting using X-ray detecting means the characteristic X-rays that have been diffracted by said sample, wherein:

said X-ray generating means is made of a plurality of metals having different atomic numbers, and generates from said respective metals a plurality of characteristic X-rays of mutually different wavelengths;

said X-ray detecting means is a pulse counting type pixel array detector, which is made of a plurality of pixels that receive characteristic X-rays of a plurality of wavelengths diffracted by said sample and that output signals corresponding to the wavelengths of said respective characteristic X-rays; and said pixels are respectively furnished with classifying means, said pixels outputting signals in different states for every wavelength of X-rays, said classifying means being adapted to classify output signals of said pixels into each of the wavelengths of the characteristic X-rays, and output the signals.

2. The wavelength-classifying type X-ray diffraction device according to claim 1, further comprising counters for counting the number of signals that have been classified by said classifying means for every wavelength.

3. The wavelength-classifying type X-ray diffraction device according to claim 1, comprising computing means for computing relational values of diffracted X-ray wavelength, diffraction angle, and intensity, on the basis of a position of diffracted X-rays detected by said X-ray detecting means, and the counted value of every wavelength of diffracted X-rays detected by said classifying means.

4. The wavelength-classifying type X-ray diffraction device according to claim 1, wherein said X-ray generating means has a rotor target made of a plurality of different metals disposed in alternating fashion along an electron scanning direction;

has a rotor target made of a plurality of different metals disposed in respectively continuous fashion along the electron scanning direction, the metals being disposed adjacently to one another in a direction perpendicular to the electron scanning direction; or has a first X-ray generating section for generating X-rays of a first wavelength, and a second X-ray generating section for generating X-rays of a second wavelength different from the first wavelength, the first X-ray generating section and the second X-ray generating section arranged at mutually different positions and respectively arranged at positions such that a given sample can be bombarded with X-rays.

5. The wavelength-classifying type X-ray diffraction device according to claim 1, wherein said X-ray detecting means is a two-dimensional pixel array detector made of a plurality of pixels lined up two-dimensionally, and having a reception surface area capable of detecting a plurality of types of diffracted X-rays of different wavelengths, or a one-dimensional pixel array detector made of a plurality of pixels lined up one-dimensionally, and having a reception length enabling a plurality of diffracted X-rays of different wavelengths to be detected.

6. The wavelength-classifying type X-ray diffraction device according to claim 1, wherein said sample is a powder sample or a single crystal sample; said X-rays of different wavelengths are Cu rays and Mo rays; the lattice constant is determined based on a diffraction profile obtained using Cu rays; and refining of the crystal structure is carried out on the basis of a diffraction profile obtained using Mo rays.

7. The wavelength-classifying type X-ray diffraction device according to claim 3, further comprising a display device for displaying the results of measurements made according to instructions from said computing means, said display device being able to display diffraction image in which a plurality of diffraction images obtained by X-rays having mutually different wavelengths are distributed in combination, and said display device also being able to display another diffraction image in which one of the plurality of diffraction images obtained by X-ray having selected single wavelength is selectively displayed.

* * * * *